(12) United States Patent
Schnute

(10) Patent No.: US 6,562,822 B2
(45) Date of Patent: May 13, 2003

(54) HETEROCYLE CARBOXAMIDES AS ANTIVIRAL AGENTS

(75) Inventor: Mark E. Schnute, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/887,226

(22) Filed: Jun. 22, 2001

(65) Prior Publication Data

US 2002/0188004 A1 Dec. 12, 2002

Related U.S. Application Data

(60) Provisional application No. 60/218,116, filed on Jul. 13, 2000.

(51) Int. Cl.[7] ............... A61K 31/495; C07D 413/02; A61P 43/00
(52) U.S. Cl. ............. 514/248; 514/255.05; 514/307; 514/311; 544/114; 544/235; 546/146; 556/180
(58) Field of Search ................ 556/180; 544/235, 544/114; 546/146; 514/248, 307, 311, 255.05

(56) References Cited

U.S. PATENT DOCUMENTS

| | | | |
|---|---|---|---|
| 5,753,666 A | 5/1998 | Beasley et al. | 514/258 |
| 5,891,878 A | 4/1999 | Beasley et al. | 514/247 |
| 5,945,431 A | 8/1999 | Jin et al. | 514/300 |

FOREIGN PATENT DOCUMENTS

| | | | |
|---|---|---|---|
| JP | 07033729 | 2/1995 | C07C/261/04 |
| JP | 08301849 | 11/1996 | C07D/217/26 |
| WO | WO97/04775 | 2/1997 | A61K/31/435 |
| WO | WO97/34894 | 9/1997 | C07D/471/06 |
| WO | WO98/11073 | 3/1998 | C07D/215/48 |
| WO | WO98/19673 | 5/1998 | A61K/31/165 |
| WO | WO99/10347 | 3/1999 | C07D/471/04 |
| WO | WO99/32450 | 7/1999 | C07D/215/56 |
| WO | WO00/40561 | 7/2000 | C07D/215/16 |
| WO | WO00/40562 | 7/2000 | C07D/215/48 |
| WO | WO00/40563 | 7/2000 | C07D/215/56 |
| WO | WO00/53610 | 9/2000 | C07D/513/04 |

Primary Examiner—Joseph K. McKane
Assistant Examiner—Andrea D. Small
(74) Attorney, Agent, or Firm—Lucy X. Yang

(57) ABSTRACT

The present invention provides a compound of formula I

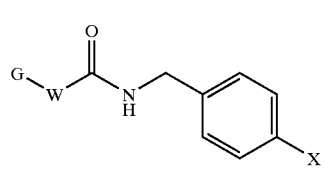

which is useful as antiviral agents, in particular, as agents against viruses of the herpes family.

21 Claims, No Drawings

HETEROCYCLE CARBOXAMIDES AS ANTIVIRAL AGENTS

CROSS REFERENCE TO RELATED APPLICATION

This application claims the benefit of the following provisional application: U.S. Ser. No: 60/218116, filed Jul. 13, 2000, under 35 USC 119(e)(i).

BACKGROUND OF THE INVENTION

1. Field of the Invention

The present invention provides heterocycle carboxamide derivatives. These compounds are useful as antiviral agents, in particular, as agents against viruses of the herpes family.

2. Technology Description

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

U.S. Pat. Nos. 5,753,666 and 5,891,878 and WO 97/04775 disclose specific 1-alkyl-substituted-quinolone-3-carboxamides that are alleged to have therapeutic utility via inhibition of Phosphodiesterase IV esterase and/or Tumor Necrosis factor activity.

Commonly assigned WO 00/40561 discloses quinolinecarboxamides as antiviral agents.

Commonly assigned WO 00/40563 discloses specific quinolinecarboxamides as antiviral agents.

Commonly assigned WO 00/53610 discloses 4-Oxo-4,7-dihydrothieno[2,3-b]pyridine-5-carboxamides as antiviral agents.

Commonly assigned WO99/32450 discloses specific 4-hydroxyquinoline-3-carboxamides and hydrazides as antiviral agents.

U.S. Pat. No. 5,945,431 discloses specific naphthyridine heterocyclic compounds having antiviral activity that are useful in the therapy and prophylaxis of cytomegalovirus (CMV) infection in mammals.

WO99/10347 discloses specific substituted 4-oxo-naphthyridine-3-carboxamides as brain receptor ligands having potential use in the treatment of central nervous system diseases and/or disorders.

WO98/19673 discloses specific heterocyclic agents for the treatment of diseases caused by viruses.

JP08301849 discloses specific heterocyclic agents useful as tachykinin receptor antagonists. They are suggested for use in treatment of the following diseases: inflammation, allergic diseases, CNS disorders, digestive system disorders, urinary tract disorders, cardiovascular diseases immunopathy. The reference suggests that the inventive compounds can be used to treat herpes, but classifies herpes as either an inflammation or allergic reaction disease. The reference does not suggest that the compounds can be used to treat infectious diseases.

JP07033729 discloses specific N-cyano-N'-substituted-arylcarboxyimidamide compounds exhibiting K+ channel opening effects and having hypotensive action and coronary vasodilating action.

WO 00/40562 discloses novel 2-oxoquinolines as selective peripheral cannabinoid receptor modulators).

WO 97/34894 dosloses Naphthyridine derivatives and their analogues inhibiting cytomegalovirus.

Despite the above teachings, there still exists a need in the art for novel compounds that demonstrate desirable antiviral activity.

BRIEF SUMMARY OF THE INVENTION

In accordance with the present invention, novel compounds which demonstrate antiviral activity are provided. More specifically, the compounds are specific heterocycle carboxamide derivatives which are useful as antiviral agents, particularly against herpes viruses.

Even more specifically, the present invention provides a compound of formula I,

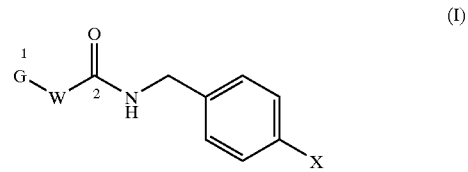

(I)

wherein,

X is Cl, Br, F, CN or $NO_2$;

G is (a) $C_{3-7}$alkyl which is partially unsaturated and is substituted by hydroxy, or (b) $C_{1-7}$alkyl substituted by $NR^1R^2$ or 4-tetrahydropyran;

$R^1$ is $C_{2-7}$alkyl substituted by hydroxy, $C_{1-4}$alkoxy, aryl, or heteroaryl;

$R^2$ is hydrogen or $C_{1-7}$alkyl;

or $R^1$ and $R^2$ together with the nitrogen to which they are attached form morpholine which may be optionally substituted by aryl or $C_{1-7}$alkyl;

W is

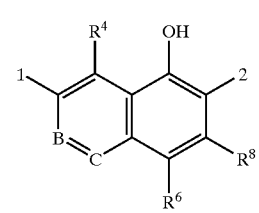

w

B is $CR^5$ or nitrogen;

C is $CR^6$ or nitrogen;

with the provisos that B and C cannot be both nitrogen;

$R^4$ is H, halogen, or $C_{1-4}$alkyl optionally substituted by one to three halogens;

$R^5$ is
(a) H,
(b) halo,
(c) $OR^{12}$,
(d) $SR^{12}$,
(e) $C_{1-7}$alkyl which may be partially unsaturated and optionally substituted by one or more substituents selected from $OR^{12}$, $SR^{12}$, $NR^{10}R^{11}$, or halo,
(f) $C_{3-8}$cycloalkyl which may be partially unsaturated and is optionally substituted by one or more substituents selected from halogen, $OR^{12}$ $SR^{12}$, or $NR^{10}R^{11}$,
(g) (C=O)$R^9$,
(h) S(O)$_m R^9$,
(i) (C=O)$OR^2$,
(j) $NHSO_2R^9$,
(k) nitro, or
(l) cyano;

$R^6$ is
(a) H,
(b) halo,
(c) aryl,
(d) het, or
(e) R7;

$R^7$ is
(a) $OR^{12}$,
(b) $SR^{12}$,
(c) $C_{1-7}$alkyl which may be partially unsaturated and optionally substituted by one or more substituents selected from $OR^{12}$, $SR^{12}$, $NR^{10}R^{11}$, aryl, halo, $C_{3-8}$cycloalkyl optionally substituted by $OR^{12}$, or het attached through a carbon atom,
(d) $NR^{10}R^{11}$,
(e) $C_{3-8}$cycloalkyl which may be partially unsaturated and is optionally substituted by one or more substituents selected from halogen, $OR^{12}$, $SR^{12}$, or $NR^{10}R^{11}$,
(f) (C=O)$R^9$,
(g) S(O)$_m R^9$,
(h) (C=O)$OR^2$,
(i) $NHSO_2R^9$,
(j) nitro, or
(k) cyano;

$R^8$ is
(a) H,
(b) $C_{1-7}$alkyl which may be partially unsaturated and optionally substituted by one or more substituents selected from $OR^{12}$, $SR^{12}$, $NR^{10}R^{11}$, or halo,
(c) $OR^{12}$, or
(d) $SR^{12}$;

$R^9$ is
(a) $C_{1-7}$alkyl,
(b) $NR^{10}R^{11}$,
(c) aryl, or
(d) het, wherein said het is bound through a carbon atom;

$R^{10}$ and $R^{11}$ are independently
(a) H,
(b) aryl, (c) $C_{1-7}$alkyl which may be partially unsaturated and is optionally substituted by one or more substituents selected from $CONR^2R^2$, $CO_2R^2$, het, aryl, cyano, or halo,
(d) $C_{2-7}$alkyl which may be partially unsaturated and substituted by one or more substituents selected from $NR^2R^2$, $OR^2$, or $SR^2$,
(e) $C_{3-8}$cycloalkyl which may be partially unsaturated and is optionally substituted by one or more substituents selected from halogen, $OR^2$, $SR^2$, or $NR^2R^2$, or
(f) $R^{10}$ and $R^{11}$ together with the nitrogen to which they are attached form a het;

$R^{12}$ is
is (a) H,
(b) aryl,
(c) het
(d) $C_{1-7}$alkyl optionally substituted by aryl, het, or halogen,
(e) $C_{2-7}$alkyl substituted by $OR^2$, $SR^2$, or $NR^2R^2$, or
(f) $C_{3-8}$cycloalkyl which may be partially unsaturated and is optionally substituted by one or more substituents selected from halogen, $OR^2$, $SR^2$, or $NR^2R^2$;

each m is independently 1 or 2;

aryl is a phenyl radical or an ortho-fused bicyclic carbocyclic radical wherein at least one ring is aromatic, and aryl maybe optionally substituted with one or more substituents selected from halo, OH, cyano, $NR^2R^2$, $CO_2R^2$, $CF_3$, $C_{1-6}$alkoxy, and $C_{1-6}$ alkyl which maybe further substituted by one to three $SR^2$, $NR^2R^2$, $OR^2$, or $CO_2R^2$ groups;

het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, $CO_2R^2$, $CF_3$, $C_{1-6}$alkoxy, oxo, oxime, and $C_{1-6}$ alkyl which may be further substituted by one to three $SR^2$, $NR^2R^2$, $OR^2$, or $CO_2R^2$ groups;

halo or halogen is F, Cl, Br, I;

1 represents the point of attachment between W and G;

2 represents the point of attachment between W and the carbonyl group of Formula (I);

and a pharmaceutically acceptable salt thereof.

In particularly preferred embodiments, X is Cl and G is 4-morpholinylmethyl.

Another embodiment of the present invention provides a pharmaceutical composition comprising a compound of formula (I) as defined above, or a pharmaceutically acceptable salt thereof, and a pharmaceutically acceptable carrier. In preferred embodiments, the composition preferably comprises a therapeutically effective amount of the compound or salt.

Still another embodiment of the present invention provides a method for treating a disease or condition in a mammal caused by a viral infection, particularly a herpes viral infection, comprising administering to the mammal a therapeutically effective amount of a compound of formula (I) or a pharmaceutically acceptable salt thereof. For this embodiment, in addition to the compounds encompassed by formula (I), G can also represent $C_{1-7}$alkyl which is fully saturated and is substituted by hydroxy.

A further embodiment of the present invention comprises the use of a compound of formula (I) or a pharmaceutically acceptable salt thereof to prepare a medicament for treating or preventing diseases or disorders caused by a viral infection, and particularly a herpes viral infection.

A final embodiment of the present invention comprises a method for inhibiting a viral DNA polymerase, comprising contacting (in vitro or in vivo) the polymerase with an effective inhibitory amount of a compound of formula (I) or a pharmaceutically acceptable salt thereof.

An object of the present invention is to provide novel compounds having biological activity.

A further object of the present invention is to provide novel pharmaceutical compositions.

Still another object of the present invention is to provide a method for treating a disease or condition in a mammal caused by a viral infection, particularly a herpes virus infection.

Another object of the present invention is to provide a method for inhibiting a viral DNA polymerase.

These, and other objects, will readily be apparent to those skilled in the art as reference is made to the detailed description of the preferred embodiment.

DETAILED DESCRIPTION OF THE PREFERRED EMBODIMENT

In describing the preferred embodiment, certain terminology will be utilized for the sake of clarity. Such terminology is intended to encompass the recited embodiment, as well as all technical equivalents which operate in a similar manner for a similar purpose to achieve a similar result.

1. Terminology Definitions

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g., 1, 2, 3, or 4) double or triple bonds in the chain.

Aryl denotes a phenyl radical or an ortho-fused bicyclic carbocyclic radical wherein at least one ring is aromatic. Het is a four- (4), five- (5), six- (6), or seven- (7) membered saturated or unsaturated ring containing 1, 2 or 3 heteroatoms selected from the group consisting of non-peroxide oxygen, sulfur, and nitrogen, which is optionally fused to a benzene ring, or any bicyclic heterocyclic group. Het includes "heteroaryl", which encompasses a radical attached via a ring carbon of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula (I) having any combination of the values, specific values, more specific values, and preferred values described herein.

Mammal denotes human and animals, specifically including food animals and companion animals.

2. The Invention

The present invention comprises compounds of formula (I) as defined above, and their pharmaceutically acceptable salts.

For the compounds of formula (I), alkyl can be methyl, ethyl, propyl, isopropyl, butyl, iso-butyl, sec-butyl, pentyl, 3-pentyl, hexyl, heptyl, etc.; $C_{3-8}$cycloalkyl can be cyclopropyl, cyclobutyl, cyclopentyl, cyclohexyl, cycloheptyl, or cyclooctyl; alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; het can be azetidinyl, 3,3-dihydroxy-1-azetinyl, pyrrolidino, piperidino, morpholino, thiomorpholino, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When alkyl is partially unsaturated, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

Specific examples of W include,

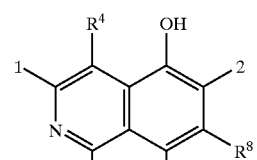

W2.1

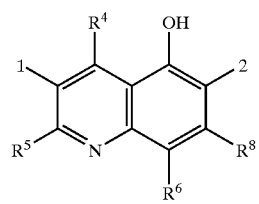

W2.2

Particularly preferred compounds are those where X is Cl and G is 4-morpholinylmethyl.

Examples of the present invention include, but are not limited to the following:

N-(4-chlorobenzyl)-5-hydroxy-3-(4-morpholinylmethyl)-6-isoquinolinecarboxamide;

N-(4-chlorobenzyl)-5-hydroxy-3-(tetrahydro-2H-pyran-4-ylmethyl)-6-isoquinoline-carboxamide;

N-(4-chlorobenzyl)-5-hydroxy-3-(3-hydroxy-1-propynyl)-6-isoquinolinecarboxamide;

N-(4-chlorobenzyl)-5-hydroxy-3-(4-morpholinylmethyl)-6-quinolinecarboxamide;

or a pharmaceutically acceptable salt thereof.

Representative examples of the synthesis of compounds falling within the scope of formula W as follows.

The following Charts A–D describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

W2.1. 5-Hydroxy-6-isoquinolinecarboxamides. Preparation of specific examples of heterocycle W2.1 follows an established literature precedent set forth in *Tetrahedron* 1973, 29, 857. and elaborated on in Charts A and B below. Benzaldehyde A.1 is condensed with 2-amino-3,3-dimethoxy-1-propanol (*Carbohydrate Res.* 1969, 10, 35–48.) to afford the corresponding imine A.2. Cyclization of A.2 by heating the imine in a mixture of polyphoric acid (PPA) provides the isoquinoline A.3. Compound A.3 is heated in the presence of a benzylamine (e.g. 4-chlorobenzylamine, 4-bromobenzylamine, or 4-fluorobenzylamine) to provide amides of the general formula A.4. Oxidation of the benzylic alcohol with manganese (IV)oxide or other suitable oxidizing agent affords a corresponding aldehyde of the formula A.5 which undergoes reductive amination with an amine (e.g. morpholine), acetic acid, and sodium triacetoxyborohydride to provide a compound such as A.6.

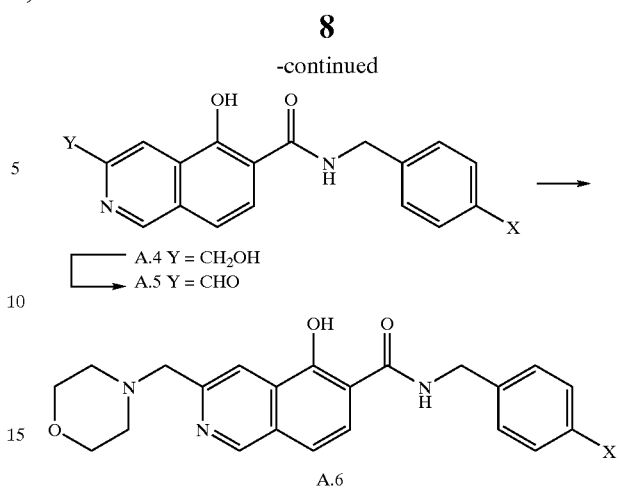

Alternatively, to prepare compounds of structure W2.1 where G=4-tetrahydro-pyranylmethyl, intermediate A.5 is protected as a methoxymethylether or other suitable phenol protecting group (Green, T. W; Wuts, P. G. M. *Protective Groups in Organic Synthesis.* Wiley, 1999) to provide B.1, Chart B. Wittig olefination between B.1 and 4-tetrahydropyranylphosphonium bromide (Bestmann, H. J.; Stransky, W.; Vostrowsky, O. *Chem. Ber.* 1979, 109, 1694–1700.) employing sodium hexamethyl-disilazide as base provides the olefin B.2. Hydrogenation of B.2 catalyzed by palladium on carbon provides B.3 by which deprotection of the phenol protecting group affords B.4. Similarly, to prepare compounds of structure W2. 1 where G=3-hydroxypropyl or 3-hydroxy-l-propynyl, intermediate B.1 is reacted with dimethoxy-diazomethylphosoniumoxide in the presence of a suitable base such as potassium tert-butoxide (*Tetrahedron Lett.* 1992, 33, 3715) to afford the corresponding acetylene of the formula C.1, Chart C. Addition of the lithium anion of acetylene C.1 prepared with lithium diisopropylamide or other suitable base to formaldehyde or a formaldehyde equivalent provides C.2 which following deprotection of the phenol affords derivatives of the formula C.3. Saturation of the alkyne by hydrogenation catalyzed by palladium on carbon in alcoholic solvents affords alkyl derivatives of formula C.4

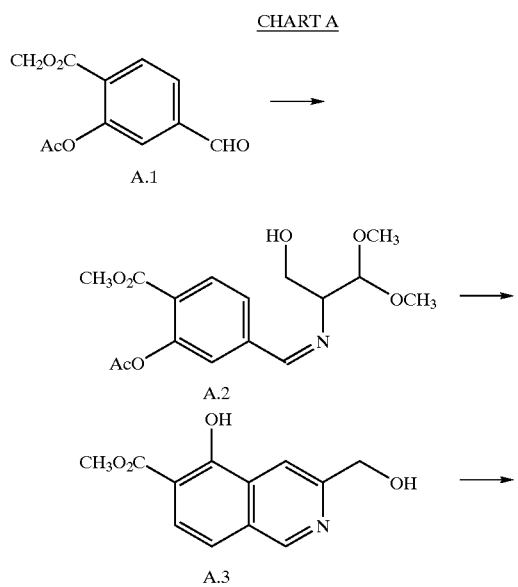

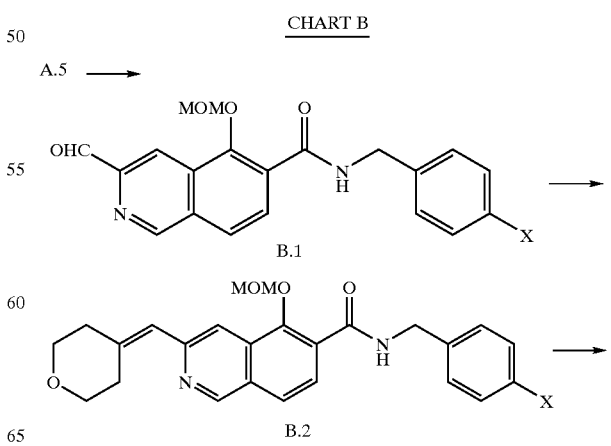

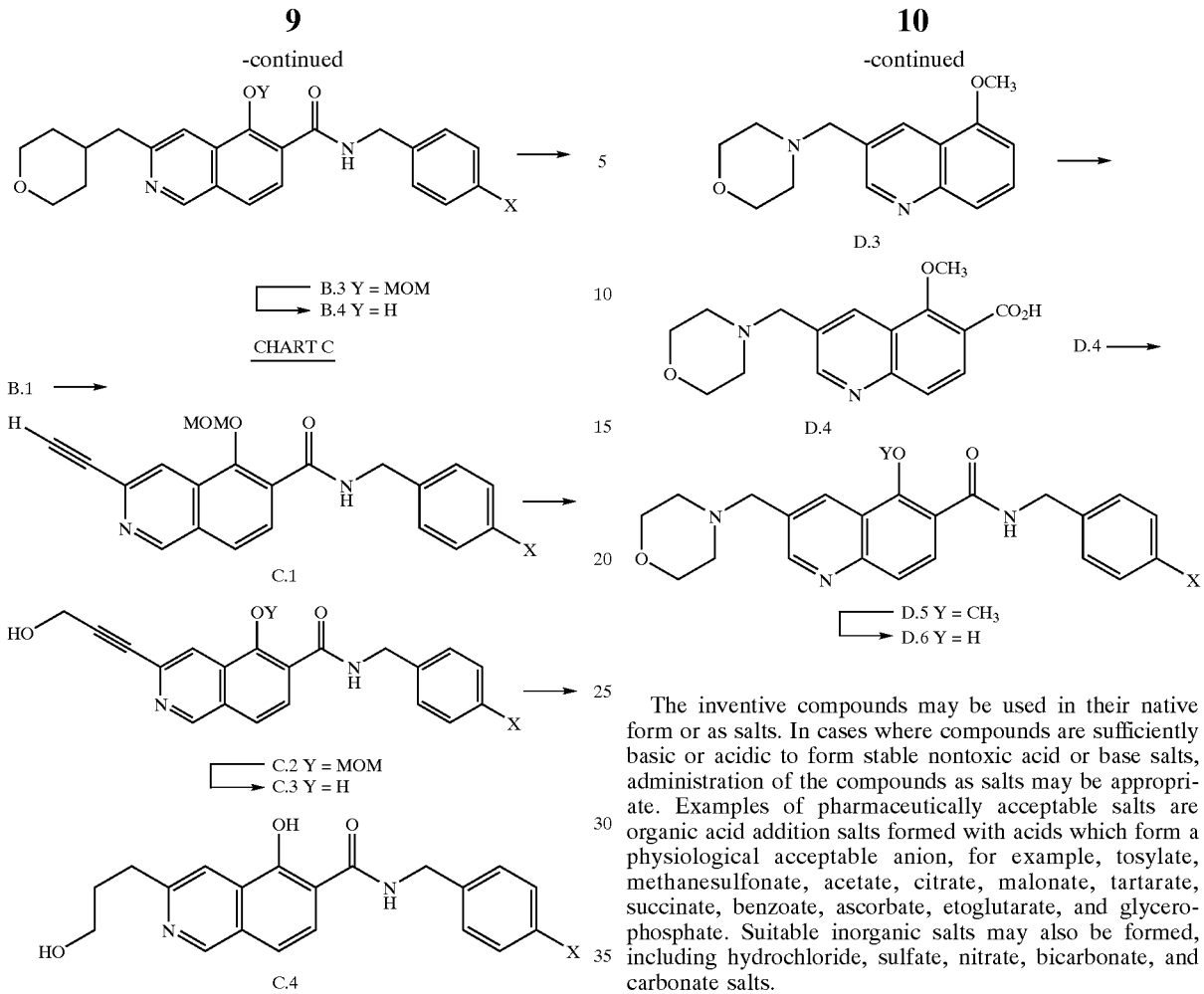

W2.2. 5-Hydroxy-6-quinolinecarboxamides. The preparation of specific examples of heterocycle W2.2. where G is 4-morpholinylmethyl is described in Chart D. Benzylic bromination of quinoline D.1 (J. M. Muchowski *J. Org. Chem.* 1991, 56, 7288–7291.) affords alkylbromide D.2. Displacement of D.2 with morpholine provides quinoline D.3. Metalation of D.3 with n-butyllithium at low temperature and trapping of the resulting anion with carbon dioxide provides carboxylic acid D.4. The resulting carboxylic acid D.4 is then coupled with a benzylamine (e.g. 4-chlorobenzylamine, 4-bromobenzylamine, or 4-fluorobenzylamine) mediated by 1,1'-carbonyldiimidazole (or other suitable carboxylic acid activating agent) to provide amides of the general formula D.5. Deprotection of the methylether by reaction with boron tribromide provides hydroxyquinolines of the formula D.6.

CHART D

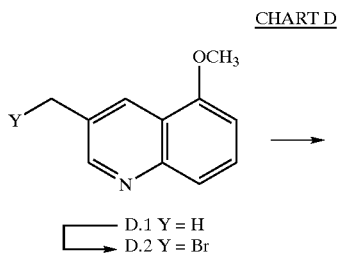

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically (including but not limited to surface treatment, transdermal application, and nasal application), intravaginally, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices such as the osmotic release type devices developed by the Alza Corporation under the OROS trademark.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr Virus, the herpes simplex virus types 1 and 2 (HSV-1 and 2), the human herpes virus types 6, 7 and 8 (HHV-6, 7, and 8) and the human cytomegalovirus (HCMV).

The invention will be further described by the following non-limiting examples.

TESTING OF INVENTIVE COMPOUNDS

The antiviral activity of a compound of the invention can be determined using pharmacological models which are well known to the art, or using the test described below.

While many of the compounds of the present invention can demonstrate activity against the CMV polymerase, these compounds may be active against the cytomegalovirus by this or other mechanisms of action. Thus, the description below of these compounds' activity against the CMV polymerase is not meant to limit the present invention to a specific mechanism of action.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 MM MgCl$_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. water bath and terminated via the addition of 40 µl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction.

Having described the invention in detail and by reference to the preferred embodiments thereof, it will be apparent that modifications and variations are possible without departing from the scope of the appended claims.

What is claimed is:

1. A compound of formula I,

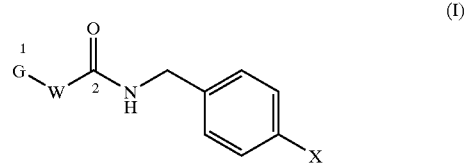

(I)

wherein,

X is Cl, Br, F, CN or NO$_2$;

G is
- (a) C$_{3-7}$alkyl which is partially unsaturated and is substituted by hydroxy, or
- (b) C$_{1-7}$alkyl substituted by NR$^1$R$^2$ or 4-tetrahydropyran;

R$^1$ is C$_{2-7}$alkyl substituted by hydroxy, C$_{1-4}$alkoxy, aryl, or heteroaryl;

R$^2$ is hydrogen or C$_{1-7}$alkyl;

or R$^1$ and R$^2$ together with the nitrogen to which they are attached form morpholine which may be optionally substituted by aryl or C$_{1-7}$alkyl;

W is

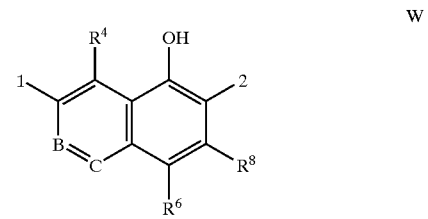

w

B is CR$^5$ or nitrogen;

C is CR$^6$ or nitrogen;

with the provisos that B and C cannot be both nitrogen;

R$^4$ is H, halogen, or C$_{1-4}$alkyl optionally substituted by one to three halogens;

R$^5$ is
- (a) H,
- (b) halo,
- (c) OR$^{12}$,
- (d) SR$^{12}$,
- (e) C$_{1-7}$alkyl which may be partially unsaturated and optionally substituted by one or more substituents selected from OR$^{12}$, SR$^{12}$, NR$^{10}$R$^{11}$, or halo,
- (f) C$_{3-8}$cycloalkyl which may be partially unsaturated and is optionally substituted by one or more substituents selected from halogen, OR$^{12}$, SR$^{12}$,or NR$^{10}$R$^{11}$, (g) (C=O)R$^9$,
(h) S(O)$_m$R$^9$,
(i) (C=O)OR$^2$,
(j) NHSO$_2$R$^9$,
(k) nitro, or
(l) cyano;

R$^6$ is
(a) H,
(b) halo,
(c) aryl,
(f) het, or
(g) R7;

R$^7$ is
(a) OR$^{12}$,
(b) SR$^{12}$,
(d) C$_{1-7}$alkyl which may be partially unsaturated and optionally substituted by one or more substituents selected from OR$^{12}$, SR$^{12}$, NR$^{10}$R$^{11}$, aryl, halo, C$_{3-8}$cycloalkyl optionally substituted by OR$^{12}$, or het attached through a carbon atom,
(d) NR$^{10}$R$^{11}$,
(e) C$_{3-8}$cycloalkyl which may be partially unsaturated and is optionally substituted by one or more substituents selected from halogen, OR$^{12}$, SR$^{12}$, or NR$^{10}$R$^{11}$,
(f) (C=O)R$^9$,
(g) S(O)$_m$R$^9$,
(h) (C=O)OR$^2$,
(i) NHSO$_2$R$^9$,
(j) nitro, or
(k) cyano;

R$^8$ is
(a) H,
(b) C$_{1-7}$alkyl which may be partially unsaturated and optionally substituted by one or more substituents selected from OR$^{12}$, SR$^{12}$, NR$^{10}$R$^{11}$, or halo,
(c) OR$^{12}$, or
(d) SR$^{12}$;

R$^9$ is
(a) C$_{1-7}$alkyl,
(b) NR$^{10}$R$^{11}$,
(c) aryl, or
(d) het, wherein said het is bound through a carbon atom;

R$^{10}$ and R$^{11}$ are independently
(a) H,
(b) aryl,
(c) C$_{1-7}$alkyl which may be partially unsaturated and is optionally substituted by one or more substituents selected from CONR$^2$R$^2$, CO$_2$R$^2$, het, aryl, cyano, or halo,
(d) C$_{2-7}$alkyl which may be partially unsaturated and is substituted by one or more substituents selected from NR$^2$R$^2$, OR$^2$, or SR$^2$,
(e) C$_{3-8}$cycloalkyl which may be partially unsaturated and is optionally substituted by one or more substituents selected from halogen, OR$^2$, SR$^2$, or NR$^2$R$^2$, or
(f) R$^{10}$ and R$^{11}$ together with the nitrogen to which they are attached form a het;

R$^{12}$ is
(a) H,
(b) aryl,
(c) het
(d) C$_{1-7}$alkyl optionally substituted by aryl, het, or halogen,
(e) C$_{2-7}$alkyl substituted by OR$^2$, SR$^2$, or NR$^2$R$^2$, or
(f) C$_{3-8}$cycloalkyl which may be partially unsaturated and is optionally substituted by one or more substituents selected from halogen, OR$^2$, SR$^2$, or NR$^2$R$^2$;

each m is independently 1 or 2;

aryl is a phenyl radical or an ortho-fused bicyclic carbocyclic radical wherein at least one ring is aromatic, and aryl maybe optionally substituted with one or more substituents selected from halo, OH, cyano, NR$^2$R$^2$, CO$_2$R$^2$, CF$_3$, C$_{1-6}$alkoxy, and C$_{1-6}$ alkyl which maybe further substituted by one to three SR$^2$, NR$^2$R$^2$, OR$^2$, or CO$_2$R$^2$ groups;

het is a four- (4), five- (5), six- (6), or seven- (7) membered saturated or unsaturated heterocyclic ring having 1, 2, or 3 heteroatoms selected from oxygen, sulfur, or nitrogen, which is optionally fused to a benzene ring, or any bicyclic heterocycle group, and het may be optionally substituted with one or more substituents selected from halo, OH, cyano, phenyl, CO$_2$R$^2$, CF$_3$, C$_{1-6}$alkoxy, oxo, oxime, and C$_{1-6}$ alkyl which may be further substituted by one to three SR$^2$, NR$^2$R$^2$, OR$^2$, or CO$_2$R$^2$ groups;

halo or halogen is F, Cl, Br, I;

1 represents the point of attachment between W and G;

2 represents the point of attachment between W and the carbonyl group of Formula (I);

and a pharmaceutically acceptable salt thereof.

2. A compound of claim 1 wherein B is nitrogen; and C is CR$^6$.

3. A compound of claim 1 wherein B is CR$^5$; and C is nitrogen.

4. The compound according to claim 1, wherein X is Cl.

5. The compound according to claim 1 wherein G is 4-morpholinylmethyl.

6. The compound according to claim 1 wherein G is 3-hydroxy-1-propynyl.

7. The compound according to claim 1 wherein G is tetrahydro-2H-pyran-4-ylmethyl.

8. The compound according to claim 1 which is selected from the group consisting of N-(4-chlorobenzyl)-5-hydroxy-3-(4-morpholinylmethyl)-6-isoquinolinecarboxamide;

N-(4-chlorobenzyl)-5-hydroxy-3-(tetrahydro-2H-pyran-4-ylmethyl)-6-isoquinoline-carboxamide;

N-(4-chlorobenzyl)-5-hydroxy-3-(3-hydroxy-1-propynyl)-6-isoquinolinecarboxamide;

N-(4-chlorobenzyl)-5-hydroxy-3-(4-morpholinylmethyl)-6-quinolinecarboxamide;

or a pharmaceutically acceptable salt thereof.

9. A pharmaceutical composition comprising a compound of claim 1 and a pharmaceutically acceptable carrier.

10. A method of treating a viral infection, comprising administering to a mammal in need of such treatment, a compound of claim 1.

11. The method according to claim 10 wherein said viral infection is a herpes virus infection.

12. The method according to claim 10 wherein said mammal is a human.

13. The method of treating viral infections comprising administering to an animal in need of such treatment, a compound of claim 1.

14. The method according to claim 10 wherein the infection is herpes simplex virus type 1 or 2, human herpes virus type, 6, 7, or 8, varicella zoster virus, human cytomegalovirus, or Epstein-Barr virus.

15. The method according to claim 10 wherein the infection is herpes simplex virus type 1 or 2, human herpes virus type 8, varicella zoster virus, human cytomegalovirus, or Epstein-Barr virus.

16. The method according to claim 10 wherein the amount administered is from about 0.1 to about 300 mg/kg of body weight.

17. The method according to claim 10 wherein the amount administered is from about 1 to about 30 mg/kg of body weight.

18. The method according to claim 10 wherein the compound is administered parenterally, topically, intravaginally, orally, or rectally.

19. A method for inhibiting a viral DNA polymerase, comprising contacting the polymerase with an effective inhibitory amount of a compound of the formula (I) according to claim 1.

20. The method of claim 19 wherein the polymerase and the compound are contacted in vitro.

21. The method of claim 19 wherein the polymerase and the compound are contacted in vivo.

* * * * *